United States Patent [19]

Grossman et al.

[11] Patent Number: 4,975,365

[45] Date of Patent: Dec. 4, 1990

[54] ASSAY FOR MEASURING DNA CELL REPAIR POTENTIAL

[75] Inventors: Lawrence Grossman; Willliam F. Athas, both of Baltimore, Md.

[73] Assignee: The John Hopkins University, Baltimore, Md.

[21] Appl. No.: 48,846

[22] Filed: May 12, 1987

[51] Int. Cl.$^5$ .......................... C12Q 1/68; C12P 19/34; C12N 15/03; C12N 15/07

[52] U.S. Cl. ........................................... 435/6; 435/29; 435/172.3; 436/63; 935/34; 935/71; 935/72; 935/82; 935/83

[58] Field of Search .......................... 435/6, 29, 172.3; 436/63; 935/34, 71, 72, 82, 83

[56] References Cited

U.S. PATENT DOCUMENTS 4,675,285  6/1987  Clark et al. .............................. 435/6

OTHER PUBLICATIONS

Protic–Sabljic, M. and Kraemer, K. H., (1985), PNAS 82, pp. 6622–6626.

Friedberg, E., (1985), *DNA Repair,* (W. H. Freeman and Co., New York, NY), pp. 505–574.

Protic–Sabljic, M. and Kraemer, K. H., (1986), Carcinogenesis, 1, No. 10, pp. 1765–1770.

Boshart et al., (1985), *Cell* 41, pp. 521–530.

*Primary Examiner*—Amelia Burgess Yarbrough
*Assistant Examiner*—Ardin H. Marschel
*Attorney, Agent, or Firm*—Cushman, Darby & Cushman

[57] ABSTRACT

A quantitative host cell reactivation assay method comprising providing a recombinant DNA plasmid containing a bacterial gene which is transiently expressed in cells to be tested for cell repair proficiency and whose respective product assay is amenable to screening; inactivating the gene so that the gene is damaged within its coding region, the inactivation being carried out directly or indirectly by a genotoxic agent, e.g. ultra-violet light, against which cell repair proficiency is to be determined; transfecting the cells to be tested with the thus inactivated gene; allowing the transfected cells to stand for a predetermined repair period; and then determining the repair efficiency of said cells by comparing the percent gene expression with the gene expression obtained when the same plasmid DNA, without inactivation is transfected into the cells. The method may be used to test repair potential in fresh human lymphocytes or in amniotic cells.

3 Claims, No Drawings

ASSAY FOR MEASURING DNA CELL REPAIR POTENTIAL

The present invention is concerned with an assay for measuring DNA cell repair potential in human lymphocytes.

BACKGROUND TO THE INVENTION

There is a growing awareness that many human cancers result from the combined effects of environmental exposure and inherent susceptibility states. Humans display a considerable range of clinical sensitivities to environmental agents such as radiation and chemical carcinogens. This variability in host response is believed to be due, at least in part, to inherent differences between individuals to repair damaged sites induced in their genetic material by many of these environmental agents. See, for example, *Individual Susceptibility to Genotoxic Agents In The Human Population*, F. J. de Serres and R. W. Pero (eds), Plenum Press, New York, pp. 321-329, 1984; *Genetic Variability in Responses to Chemical Exposure*, Banbury Report 16, G. S. Omenn and H. V. Gelboin (eds), Cold Spring Harbour Laboratory, pp. 145-154, 1984; and *Epidemiology and Quantitation of Environmental Risk in Humans from Radiation and Other Agents*, A. Castellani (ed), Plenum Press, New York, pp. 205-212, 1984.

A lowered DNA repair capability may, through an accumulation of persistence in levels of genetic damage, promote the malignant transformation of target cells within the exposed individual, and ultimately increase the likelihood that frank neoplasia occurs. In direct support of this is the marked predisposition towards sunlight-associated skin cancer seen in xeroderma pigmentosum (XP), a rare, heterogenous recessive disorder (*Clinics Derm.* 3(1):33-369, 1985). The principal biochemical abnormality expressed by XP patients is a severely reduced cellular capacity to remove DNA photo-products induced by ultraviolet radiation (UV), the primary etiologic agent in skin cancer. Variation in residual UV repair between classic XP patients (2%-60% of normal) apparently is due to a systemic genetic defect within at least eight genes or alleles controlling the initial incision step of nucleotide excision repair. See *The Inherited Basis Of Metabolic Disease*, J. B. Stanbury, J. B. Wyngaarden, D. S. Frederickson, J. L. Goldstein, and M. S. Brown (eds), McGraw-Hill Book Company, New York, pp. 1227-1248, 1983. This deficiency in the repair mechanism in XP cells also appears to be applicable to genetic damage by a variety of genotoxic drugs and chemical carcinogens and a recent report of an excess incidence of internal non-UV associated neoplasms in XP patients under age 40 (see, *Carcinogenesis,* 5(4):511-514, 1984) seems to extend the mediating effects of DNA repair to include both UV and chemically-induced forms of neoplasia.

Excision appears to be the most prevalent form of DNA repair in human cells. This comprises a series of coordinated enzymatic steps through which damaged sites are excised from DNA along with neighboring single strand regions, and the resulting gap resynthesized using the intact opposite strand as a template. Thus, through the concerted action of various cellular repair enzymes, potentially oncogenic lesions are removed from DNA and native biologic structure and function subsequently restored. As noted, this repair capability appears to be lacking in varying degrees in XP patients.

Since the initial incision of DNA near the site of damage is considered a crucial, rate-limiting step in the overall repair process, measuring the rate or extent to which a given cell population is able to incise damaged DNA, or perform any subsequent step, is generally considered indicative of repair proficiency. Although many procedures are capable of providing such measures, most require technical capabilities which preclude their use on a routine large-scale basis. Thus, existing methodology for population-based assessment of cellular repair essentially is limited to examining the extent to which UV-exposed lymphocytes incorporate the radiolabeled nucleoside, $^3$H-thymidine, into UV-damaged cellular DNA during the resynthesis step. Commonly referred to as unscheduled DNA synthesis (UDS), the assay achieves a quantitative measure through scintillation counting of intact cells or cell extracts following a post-irradiation repair incubation period. Although capable of detecting large differences (e.g., XP patient vs non-XP control), a number of confounding biochemical artifacts exist in UDS which significantly reduce the specificity with which relatively smaller differences in incorporated radioactivity (as would be expected in the general population) may reflect true differences in repair proficiency. See, *Individual Susceptibility To Genotoxic Agents in the Human Population*, de Serres et al, Plenum Press, N.Y., pages 321-329, 1984.

Furthermore, since entire cells are being irradiated, the introduction of uniform amounts of cellular DNA damage between large numbers of replicate and independent cell cultures cannot be easily controlled, thus effectively lowering both assay precision and accuracy.

For purposes of analytical epidemiologic research, a laboratory procedure for screening cellular repair proficiency optimally should be highly sensitive and specific for DNA repair; quantitative; precise; routine; and relatively inexpensive. Since UDS is deficient in several of these characteristics, with fundamental components of the assay being involved, modification of this procedure to render it appropriate for epidemiologic study is not considered feasible.

Recent advances in recombinant technology allowing for large scale molecular cloning, transfer, and expression of biologically active DNA in cultured human cells have opened up the possibility of designing procedures for measuring cell repair potential. Such techniques have been employed recently in the development of high resolution procedures for studying basic mechanisms of human DNA repair. See *Br. J. Cancer,* 49 (Suppl. VI):67-72, 1984 and *Mol. Gen. Genet.,* 195:175-179, 1984.

It has also been noted that exogenously damaged DNA, when introduced into cultured human cells, is acted upon by cellular repair enzymes. This phenomena, termed host cell reactivation (HCR), is based on findings that human "host" cells, after infection with radiation or chemically damaged (i.e., inactivated) viral particles, were capable of reactivating the inactivated virus to a biologically competent state as measured by plaque formation, viral antigen formation, cell transformation, etc. See *Adv. Rad. Biol.,* 10:1-37, 1983. The reactivation of biologic competence is taken as an indirect measure of cell ability to restore functionality to damaged regions of the viral genome, a direct consequence of DNA repair. That relative measures of viral HCR correlate reasonably well with conventional biochemical measures of repair in XP cells at varying levels of repair proficiency (see *Short-Term Tests for Chemical Carcinogens*, Stich et al, Springer-Verlag, N.Y. pages 20-35, 1981), provides strong evidence that HCR processes validly reflect the inherent host cell capacity to repair cellular DNA.

BROAD DESCRIPTION OF THE INVENTION

An important object of the invention is to provide a reliable and sensitive laboratory assay for determining cellular repair proficiency which represents an improvement over previously disclosed or available assay procedures. It is a particular object of the invention to provide a laboratory procedure for determining cellular repair proficiency which is sensitive, specific and reliable and otherwise meets requirements indicated above. A more specific object of the invention is to provide a laboratory procedure for routinely measuring DNA repair efficiency in human lymphocytes in a relatively simple and reliable way using available recombinant DNA techniques. Other objects will also be hereinafter apparent.

In its broadest aspects, the invention contemplates a quantitative host cell reactivation (HCR) assay which comprises (1) providing a recombinant DNA plasmid containing a bacterial indicator gene which is transiently expressed in cells to be tested, notably human lymphocytes, the gene being one which is inactivated directly or indirectly by a genotoxic agent for which cell repair proficiency is to be determined, e.g. by exposure to a measured amount of ultra-violet light, and which codes for, or expresses, a product amenable to screening; (2) inactivating the gene by, for example, the application of the measured amount of ultra-violet light to the plasmid so that the gene is damaged or inactivated within its coding region; (3) transfecting human lymphocytes to be tested with the plasmid containing the thus inactivated gene; (4) allowing the transfected lymphocytes to stand for a predetermined repair period; and (5) then determining the repair efficiency of the lymphocytes by comparing the percentage gene expression with the gene expression obtained when the same plasmid DNA, without inactivation, is transfected with the lymphocytes. Lymphocyte cell lines having known levels of repair proficiency may also be used to standardize inter-individual variation in terms of absolute repair.

DETAILED DESCRIPTION OF THE INVENTION

Plasmids with the appropriate indicator gene are available and any of these may be used for present purposes. It will be appreciated that the indicator gene should be one which is capable of expression in human lymphocytes and its expression product should be appropriate for quantitative screening or identification. The gene should also be one which can be inactivated by damage from ultra-violet (UV) light so that expression of the gene product in the cultured lymphocytes is an indication of the DNA repair properties of the lymphocytes. Plasmids containing the bacterial (β-gal gene or bacterial CAT gene may be mentioned as examples. These provide, as expression products, the bacterial (β-galactosidase (β-gal) enzyme and bacterial chloramphenicol acetyltransferase (CAT) enzyme.

As examples of known plasmids containing the (β-gal gene, there may be mentioned pGA293 and pCH110 (see *Mol. Cell Biol.*, 2:1628-1632, 1982 and *J. Mol. Appl. Genet.*, 2:101-109, 1983). These plasmids have been used, in accordance with the invention, in transfection experiments involving transformed lymphocyte cell lines. The β-gal assay is a colorimetric analysis, in contrast to the CAT assay which requires a radiolabeled substrate. Although an isozymic form of β-gal is known to exist in human cells, it is believed that the low endogenous levels thereof do not significantly interfere with measurements associated with transfection. Using DEAE-dextra mediated transfection as taught by McCutchan, *J. Natl. Cancer Inst.*, 41:351-356, 1968, a simple, proven chemical procedure amenable to transfecting large numbers of cell cultures, plasmid-driven β-gal expression has been achieved with pCH110. However, the activity did not reach levels where measurement could be made without complication by endogenous enzyme activity. Thus, while it may be possible to use the β-gal indicator for present purposes under some circumstances, the CAT embodiment is preferred.

The CAT embodiment may be illustrated by reference to the two plasmids pRSVCAT and pSV2CAT, which contain the bacterial CAT gene under different regulatory elements (see Gorman et al, *Proc. Natl. Acad. Sci. U.S.A.*, 79:6777-6781, 1982 and *Mol. Cell Biol.*, 2(9):1044-1051, 1982. An advantage in using a CAT plasmid over a β-gal plasmid is that no known human isozyme to CAT exists. Therefore, its assay is highly sensitive and specific for plasmid-derived CAT enzyme activity. Furthermore, in contrast to the β-gal enzyme, CAT enzyme is remarkably resistant to both protease and temperature inactivation. Thus, samples may be frozen and subsequently thawed for simultaneous assay. Results from experiments based on the CAT plasmids have consistently demonstrated that quantitative levels of CAT activity can be obtained in transformed cell lines with either CAT plasmid pRSVCAT and pSV2CAT, against a near zero background activity. Additionally, the magnitude of the signal obtained is sufficient for present purposes.

Of the CAT plasmids mentioned above, pSV2cat is a relatively small gene whose gene product, chloramphenicol acetyltransferase (CAT), is easy to assay, sufficiently immunogenic to generate good polyclonal antibodies in rabbits, and, importantly, is expressed to high levels in fibroblasts, lymphoblasts and mitogen-induced lymphocytes. Because there is no readily available in situ assay to quantitate the percent of transfected cells in any cellular population, there may also be used a separate gene system such as pSVgpt whose gene product, xanthine guanine phosphoribosyl transferase (XPRT), can be assessed catalytically either in situ or in vitro, or immunologically for crossreacting materials generated after repair.

Another option is to use pSV2CATpSVGPT which has tandem expressible genes that possess all the advantages of pSV2CAT and pSVGPT. Assuming that the size difference does not influence the dosimetry of the plasmid, this plasmid (i.e. pSV2CATpSVGPT) permits (a) in situ evaluation of the efficiency of transfection by following XPRT activity by autoradiography of [$^3$H]-xanthine uptake into nuclei; and (b) the temporal repair of the gpt gene either by in vitro assay of CAT activity or immunologically by measuring crossreactivating materials (CRM) for either CAT or GPT proteins. Another CAT plasmid which may be mentioned for possible use herein is pCMV CAT. The nucleotide sequence of the DNA enhancer/promoter of this plasmid is disclosed in *Cell* 41, 521–530 (1985) by Boshart et al.

The selected plasmids may be propagrated for use in any convenient fashion. In one preferred way, the plasmids are propagated in *E. coli* strain HB101 and isolated in large scale by standard molecular cloning techniques involving Tritonlysozyme lysis and double banding in cesium chloride. All such preparations should be subsequently checked for purity, for example, by gel electrophoresis and should display greater than 90% super-coiled forms to be used for transfection.

The coding gene of the plasmid DNA may be damaged or inactivated by exposure to UV irradiation or equivalent means, e.g. chemically. The invention thus contemplates the use of any genotoxic agent which can inactivate the gene and for which DNA repair proficiency is to be determined. This agent may be either a direct inactivating agent such as UV light or alkylation agent or an indirect inactivating agent, for example, a polycyclic hydrocarbon. The indirect inactivating agents require pre-incubation with metabolic activating systems such as rat liver microsomes. If desired, the indicator gene may be isolated from the plasmid, damaged and then reinserted into the plasmid for transfection. Preferably, however, the intact plasmid itself is subjected to light or other damaging means to inactivate the gene. The optimum amount of light or its equivalent so used to inactivate the selected gene can be readily determined by straightforward experimentation.

The invention may be used to determine the cell repair characteristics of human or other animal cells, particularly lymphocytes. Any such lymphocytes (fresh or cryopreserved) may be used although cultured peripheral blood lymphocytes stimulated by phytohemagglutin (PHA) (i.e. mitogen-stimulated) are preferred. To this end, the blood cells are isolated, exposed to PHA, and then cultured for varying lengths of time prior to transfection. Data indicates that mitogen-stimulated primary lymphocytes are capable of DNA uptake and quantitative gene expression.

Conditions for PHA activation, culturing and transfecting primary cells will vary but optimums can be experimentally determined. Lymphocytes for testing may be obtained from blood specimens collected from any human or animal source requiring a determination of cell repair efficiency. The lymphocytes are advantageously isolated from the specimens using standard buoyant density centri-fugation techniques (Ficoll-Hypaque) within six hours of specimen collection to insure optimal viability and response to mitogen. The washed lymphocytes are suspended at a cell density of $1-1.2 \times 10^6$ cells per ml in RPMI-1640 media with 10–20% sera, antibiotics and mitogen (PHA). Mitogen-stimulated lymphocytes are then grown in stationary suspension culture as above, and transfected within 24–72 hours.

Transfection of cultured human lymphocytes, according to the invention, may be accomplished in various ways. Preferably, however, the lymphocytes are transfected by standard DEAE-dextran mediated methods as known in the art. This technique has been successfully used to reproduce yields close to 80% transient expression of the CAT gene in both EBV-transformed and PHA-stimulated human lymphocytes and independent call cultures. The procedure essentially involves 10–15 minute exposure to plasmid DNA/-DEAE-dextran in RPMI-1640 media without sera, then the cells are subsequently shocked for two minutes with HEPES-buffered saline (HBS) containing 10% dimethylsulfoxide (DMSO), washed and returned to culture.

The transfection is followed by a post-transfection DNA repair period after which the lymphocyte culture are harvested, lysed and the cell-free extract assayed both for total protein content and gene product. Typically the post-transfection repair period is from 24–48 hours after which the cells are collected by centrifugation, washed twice with PBS, and lysed by three cycles of freeze-thawing. Cell debris is cleared by centrifugation and the cell-free extract then assayed, as noted, for total protein content and CAT gene product. Absolute repair capacity is expressed in terms of the percent gene expression reactivated in cells receiving damaged plasmid relative to basal expression levels in parallel control cells transfected with non-damaged plasmid DNA. Variation in absolute repair capacity between independent cell cultures (individuals) are standardized by normalizing all values obtained respective to a standard repair curve constructed with repair-deficient XP cells and presumed repair-proficient lymphocyte cell lines.

According to one embodiment of the invention, the selected plasmid, e.g. pSV2CAT or pRSVCAT, after inactivation or damage by exposure to UV-light, is introduced into $5 \times 10^5$ lymphocytes to be tested through the combined action of DEAE followed by DMSO shock and thereafter (e.g. 48 hours or so later) scored for production of active gene product. Polyclonal antibodies may be used to assess the amount of gene product followed by phosphatase-linked counter antibodies. The level of nascent protein may also be compared to cells transfected with undamaged vectors as well as the level of repair in internal standard lymphoblasts derived from differing xeroderma pigmentosum complementation groups with known levels of DNA repair capabilities. These XP cells may be run in parallel with each set of experimental lymphocytes as internal standards.

Cells having known repair capacities are available for use as assay standards. For example, Epstein-Baar virus (EBV) transformed lymphobastoid cell lines derived from various XP homozygotes, heterozygotes and presumed normals are available (e.g. from the Institute for Medical Research, Camden, N.J.) and represent relative repair capacities from less than 2% up to 100% of normal. Since these cells grow indefinitely in culture and may effectively be stored through cryopreservation, they are an optimal source of internal assay standards. These cells are routinely propagated in stationary suspension culture with RPMI-1640 media containing 10–20% sera, at 37° C. in a humidified atmosphere of 5% $CO_2$. Stock cultures are kept in proliferative growth by maintaining viable cell densities as $0.8-1.2 \times 10^8$ cells per ml. Aliquots of stock cultures are seeded at lower densities 2–4 days prior to transfection to insure optimal growth conditions for gene transfer.

The assay used to determine cell repair proficiency necessarily depends on the nature of the indicator gene used in the recombinant DNA plasmid expression which is used to transfect the test cells. Where the plasmid contains the CAT gene, as in the case of pSV2CAT or pRSVCAT, conventional CAT enzyme assays may be used. Chloramphenicol acetyltransferase (CAT) is a bacterial enzyme that catalyzes the transfer of acetyl groups to the antibiotic chloramphenicol. The standard assay for measuring CAT enzvme activity in transfected eukaryotic cells measures the extent (or rate) of acetylation of $^{14}C$-labeled chloramphenicol using acetyl coenzyme A as a acetyl group donor. Following reaction incubation at 37° C., chloramphenicol and its acetylated products are extracted into ethyl acetate, separated by thin-layer chromatography, and visualized by autoradiography. For quantitative assessment, acetylated products spots are cut from the thin layer plate, and radioactivity determined by liquid scintillation counting. This assay exhibits a less than 10% coefficient of variation, and has proven very reliable. However, it also is fairly lengthy when large numbers of samples are run (approximately 3 days), and involves a number of simple, yet rather tedious steps.

As an alternative CAT assay, there may be mentioned a relatively recent method (*Anal. Biochem.*, 156:251–256, 1986) which employs acetyl coenzyme A radiolabeled with $^{14}$C or tritium in the donor acetyl group, and is essentially similar to the above described method except that it requires no chromatographic or autoradiographic step. Following reaction incubation at 37° C., radiolabeled acetylated products are extracted into ethyl acetate and directly counted by liquid scintillation counting. Instead of 3 days time, numerous steps and supplies, the assay reduces to an approximate 4 hour procedure, capable of providing quantitative results the same day as cell harvest. In addition, intra-assay coefficient of variation of less than 5% is reported.

It will be recognized that various alternatives or modifications may be used in the present invention for determining or highlighting the degree of reactivated gene expression. Such techniques as DMSO shock, heparin rinse or chloroquine incubation are known in the art to be useful for increasing the transient expression levels of transfected plasmid DNA in the mammalian cells and the optimal use of such techniques in both test and reference specimens is contemplated for present purposes.

Advantageously culture and transfection conditions are selected to minimize the amount of lymphocytes required for test purposes. It appears that as few as $5.0 \times 10^5$ to $1.0 \times 10^6$ lymphocytes, roughly 10 ml. of whole blood, or even lower, may be used although it will be recognized that more or less than this number of lymphocytes may be used.

As indicated earlier, lymphocytes for use herein in the practice of the present assay may be stored by cryopreservation until they are to be used. The use of lymphocyte cryopreservation to study DNA repair offers a number of advantages including, for example, the elimination of variance in the outcome measure due to inter-assay variation, since all samples may be cultured and assayed simultaneously.

The invention is illustrated, but not limited, by the following example:

EXAMPLE

Discarded diagnostic blood specimens are used as the source of primary blood mononuclear cells for test purposes according to this example. Lymphocytes are isolated using standard buoyant density centrifugation techniques (Ficoll-Hypaque) within six hours of specimen collection to ensure optimal viability and response to mitogen. The washed lymphocytes are suspended at a cell density of $1.0-1.2 \times 10^6$ cells/ml in RPMI-1640 media with 10–20% sera, antibiotics, and PHA. Mitogen-stimulated lymphocytes are then grown in stationary suspension culture and transfected within 72 hours.

Immediately before treatment with the inactivating or genotoxic agent, e.g., UV light, plasmid DNA is diluted with sterile distilled water to 50 µg/ml, and transferred into a sterile plastic 60mm tissue culture dish placed on ice. Irradiation is performed with a standard bactericidal lamp at 254 ηm, and a fluence rate of approximately 2 Joules/m$^2$ per sec. At this wavelength, the predominant form of DNA damage is the pyrimidine dimer photoproduct, the prototype test lesion used in experimental DNA repair studies of XP. UV dose is varied between 0 and 1000 Joules/m$^2$ to determine the doses at which normal peripheral blood lymphocytes restore approximately 80% control CAT activity during times when CAT gene is maximally expressed.

After UV exposure (or equivalent treatment with another genotoxic agent) treatment, plasmid DNA is introduced into cultured lymphocytes by DEAE-dextran mediated procedure as described by McCutchan et al, *J. Natl. Cancer Inst.*, 41:351–356, 1968. The basic process involves resuspending approximately $5 \times 10^6$ cells in 3 ml of serum-free RPMI-1640 media containing plasmid DNA (1 µg/ml), DEAE-dextran (150 µg/ml), and 50mM Tris-HCl, pH 7.3. After incubation at 37° C. for 15 minutes, the cells are gently centrifuged, washed twice in media containing 10% sera, and returned to their original culture media supplemented 1:1 with fresh complete media without PHA.

For determining CAT enzyme activity, cells are harvested, washed twice with phosphate-buffered saline (PBS), and lysed by 3 cycles of freeze-thawing in ethanol/dry ice and 37° C. water bath. Cell debris is then cleared by centrifugation and the cell-free extract immediately assayed for total protein content and CAT activity. Alternatively, cell-free extracts are quick-frozen and stored at $-70°$ C. for future assay (within two weeks). In preliminary studies of both transformed and primary cells, the expression of CAT activity is noted as measurable at 24 hours, reaches a maximum at approximately 48 hours, then subsequently diminishes. The plasmid HCR assay measures extents of reactivation; therefore, cells are harvested at 48 hours, at which time CAT activity is maximal, and thus most accurately quantified.

Following reaction incubation at 37° C., chloramphenicol and its acetylated products are extracted into ethyl acetate, separated by thin-layer chromatography, and visualized by autoradiography. For quantitative assessment, acetylated products spots are cut from the thin layer plate, and radioactivity determined by liquid scintillation counting. This assay exhibits a less than 10% coefficient of variation.

As an alternative to the above noted chromatographic process, the following CAT assay procedure, based on solubility differences rather than chromatography, may be used:

After the reaction incubation at 37° C., radiolabeled acetylated products are extracted into ethyl acetate and directly counted by liquid scintillation counting. This assay reduces the time involved and is capable of providing quantitative results the same day as cell harvest. In addition, an intra-assay coefficient of variation of less than 5% appears to be obtainable.

CAT enzyme activity is determined as a rate in terms of moles chloramphenicol acetylated/min/mg protein. Total cell extract protein is determined using the Bradford protein assay (*Anal. Biochem.*, 72:248–254, 1976), with bovine serum albumin (BSA) employed as a standard. The Bradford assay is a simple colorimetric analysis, and displays less than a 5% coefficient of variation between multiple replicate samples.

The CAT activity results obtained on culturing the UV-damaged plasmid DNA are then compared with the activity shown when a similar batch of lymphocytes is transfected with the undamaged plasmid DNA. If the activity obtained with the UV-damaged plasmid DNA is below 80% of that obtained with the undamaged plasmid DNA, it can be concluded that the DNA involved lacks adequate UV repair characteristics.

While the plasmid pSV2CAT has been used in the foregoing example to illustrate the invention, it is to be noted that other similar CAT plasmids, such as pRSVCAT may also be used in the same way to transfect both transformed and primary human lymphocytes for the purpose of determining cell repair potential of lymphocytes. Other plasmids which function in similar fashion may also be used. Plasmids harboring the CAT gene (pU3R-I, pU3R-8, pU3R-III), but containing regulatory elements derived from the lymphotrophic virus HTLV-III, recently have been shown to direct 2-4 times higher levels of CAT in transformed human lymphocyte cell lines (Science, 225:381-385, 1984; and Science, 227:171-173, 1985) and it is contemplated that such plasmids could also be used for present purposes. Plasmids selected should be such as to permit a useful level of CAT expression in primary cells, preferably the highest possible transient level of such expression, for use in subsequent UV-inactivation tests.

The extent of the use of the present assay depends on various factors. For example, the cultured lymphocytes or cells which are employed must be capable of plasmid DNA uptake and gene expresison. Although substantial inter-individual variation in control CAT expression levels is likely to occur (40%-60%) repair proficiency is not likely to be effected given that all outcomes are based on relative measures (i.e., repair proficiency in terms of % CAT reactivated relative to control CAT level). This may be checked by running the plasmid HCR assay with varying concentrations of DNA on respective replicate single source cell cultures. If the repair assay outcome measure is not fairly stable relative to input DNA, or if significant numbers of independent cell cultures are simply refractory to DEAE-dextran mediated transfection, alternative gene transfer methods need to be considered.

Inter-individual variation in lymphocyte response to mitogen has been noted in numerous experimental and population-based studies. The effect of this variability may have upon inter-individual variation in DNA repair proficiency, as measured by plasmid HCR, is not yet determined. Studies of DNA repair have shown that mitogenstimulated lymphocytes incorporate higher levels of tritiated thymidine than non-stimulated cells. However, the exact biochemical nature of this increased incorporation is also unknown. Since only cells which have undergone blastogenesis contribute to the outcome measure in the plasmid HCR assay (i.e., will be expressing CAT enzyme activity), it is believed that variability in mitogenic response, as with transfection efficiency, will only compromise the present method in the field if significant numbers of cell cultures simply fail to activate. Application of the plasmid HCR assay within certain select cancer populations, such as lung cancer patients, where mitogenic response is known to be abnormal, thus may not be feasible or particularly meaningful.

As will be evident, the assay of the invention is based on the use of recombinant DNA plasmid expression vectors, small circular segments of primarily bacterial DNA, which harbor the necessary base sequences allowing for transient expression of a resident indicator gene in cultured human cells. Using standard molecular cloning procedures, large numbers of a respective plasmid are propagated, the associated gene function inactivated by a quantifiable amount of UV-induced DNA damage or the equivalent, and the irradiated plasmid DNA transferred into cultured cells. By employing a gene whose respective gene product is readily assayable in human cells (e.g. hormones, enzymes), monitoring restoration of gene function thus simplifies to routine laboratory assay. Restricting the indicator to one which is not normally found in human cells, or only at low endogenous levels, further guarantees a high level of sensitivity.

In a preferred embodiment, the recombinant plasmid contains the CAT indicator gene and this is transferred into PHA-stimulated peripheral blood lymphocytes by DEAE-dextran mediated transient expression techniques. Following a post-transfection DNA repair period, lymphocytes are harvested and the cells assayed for CAT enzyme activity. Absolute repair proficiency may be expressed in terms of the percent CAT enzyme activity reactivated in cells receiving UV-damaged plasmid, relative to control activity levels in parallel cells receiving the non-damaged plasmid. Variation in absolute repair capacity between independent cell cultures (i.e., individuals) are standardized by normalizing all absolute values relative to internal standards of known repair proficiency, provided, for example, by transformed XP and non-XP Lymphocyte cell lines.

The term "transfected" is used herein in conventional manner to indicate the introduction of exogenous donor DNA into recipient cells.

The present assay is of broad application for determining cell repair potential. For example, it may be used to check the repair potential of individuals whose occupation environmentally may subject them to risks of cancer. Typically this includes watermen or other individuals whose exposure to sunlight may be the cause of skin or lip cancer as in the case of XP. Alternatively, the assay may be used to check against the effects of exposure to alkylating agents, aromatic hydrocarbons or the like as may be encountered in petroleum cracking, dump sites or similar environmental problem areas. While the invention is particularly described above with respect to testing in fresh human lymphocytes, it is to be noted that amniotic cells may also be tested according to the invention against amiocentesis. This last mentioned type of testing may be used for genetic counselling.

In brief, the invention provides a quantitative host cell reactivation (HCR) assay of DNA repair in cultured peripheral blood lymphocytes, amniotic cells or the equivalent, utilizing damaged or inactivated recombinant DNA plasmid expression vectors for assay purposes. Various modifications, however, may be made in the invention as described. Accordingly, the scope of the invention is defined in the following claims wherein:

What is claimed:

1. A quantitative host cell reactivation assay method comprising providing a recombinant DNA plasmid containing a bacterial gene which is transiently expressed in human lymphocytes to be tested and whose product essay is amenable to screening; inactivating said gene by exposure to ultra-violet light so that the gene is damaged within its coding region; contacting the lymphocytes to be tested with the thus inactivated gene and with diethylaminoethane (DEAE)-dextran under conditions such that transfection of said lymphocytes with the thus inactivated gene is effected; allowing the transfected lymphocytes to stand for a predetermined repair period; and then determining the repair efficiency of said lymphocytes by comparing the percent gene expression with the gene expression obtained when the same plasmid DNA, without inactivation is transfected into said lymphocytes.

2. The method of claim 1 wherein the indicator gene codes for an enzyme.

3. The method of claim 2 wherein the plasmid is a CAT plasmid.

* * * * *